United States Patent [19]

Eguchi et al.

[11] Patent Number: 4,705,403
[45] Date of Patent: Nov. 10, 1987

[54] APPARATUS AND METHOD FOR MEASURING A PHOTOMETRIC CHARACTERISTIC OF A SAMPLE PORTION

[75] Inventors: Ken Eguchi, Yokohama; Yukuo Nishimura, Sagamihara; Masahiro Haruta, Funabashi; Hiroshi Matsuda, Yokohama; Yutaka Hirai; Takashi Nakagiri, both of Tokyo, all of Japan

[73] Assignee: Canon Kabushiki Kaisha, Tokyo, Japan

[21] Appl. No.: 712,026

[22] Filed: Mar. 15, 1985

[30] Foreign Application Priority Data

| Mar. 21, 1984 | [JP] | Japan | 59-53979 |
| Mar. 21, 1984 | [JP] | Japan | 59-53980 |
| Mar. 21, 1984 | [JP] | Japan | 59-53981 |
| Mar. 21, 1984 | [JP] | Japan | 59-53982 |
| Mar. 21, 1984 | [JP] | Japan | 59-53983 |

[51] Int. Cl.⁴ .................. G01J 3/42; G01N 21/27
[52] U.S. Cl. ............................. 356/319; 356/326; 356/444
[58] Field of Search .................. 356/444, 319, 326

[56] References Cited

U.S. PATENT DOCUMENTS

| 4,118,781 | 10/1978 | Brezinski et al. | 356/444 |
| 4,150,899 | 4/1979 | Nakamura | 356/444 |
| 4,549,809 | 10/1985 | Minekane et al. | 356/444 |

Primary Examiner—Vincent P. McGraw
Attorney, Agent, or Firm—Fitzpatrick, Cella, Harper & Scinto

[57] ABSTRACT

A photometric apparatus includes a light source, apparatus for oscillating a light beam spot across a sample, apparatus for measuring secondary light from the sample, and apparatus for determining the specific portion of the sample to be examined by photometry. With this photometric apparatus, each of a plurality of microscopic areas of the sample can be evaluated accurately.

9 Claims, 10 Drawing Figures

APPARATUS AND METHOD FOR MEASURING A PHOTOMETRIC CHARACTERISTIC OF A SAMPLE PORTION

BACKGROUND OF THE INVENTION

1. Field of the Invention

The present invention relates to an apparatus and method for measuring transmitted light, reflected light, phosphorescence, or luminescence from a substance to examine physical properties, superficial condition, or compositional state of the substance.

2. Description of the prior Art

Aiming at surpassing conventional electronics, there have been introduced recently new techniques of molecular electronic devices and bio-chips wherein a molecule or an assembly of a small number of molecules functions as an electronic element. Among such new techniques, the method of forming a film of monomolecular layer(s) draws attention as a technique of organizing a highly ordered laminar assembly of molecules. This method comprises transferring a monomolecular layer formed on a wafer surface onto a solid surface, or building up such monomolecular layers one by one over a solid surface, thereby forming an ultra thin film. According to this method, the components and structure of the composite film can be freely designed. In order to evaluate absorption spectra of coloring matter in such monomolecular films, an extremely slight change in transmittance must be detected and therefore special photometric apparatuses are in use.

FIG. 5 illustrates such a photometric apparatus according to the prior art. In operating this apparatus, a sample held in a sample cell 3 is irradiated through a spectroscope 2 with a light beam from a light source 1 while oscillating the sample 4 in the direction perpendicular to the light beam by means of an oscillation regulating unit 5, the transmitted light is received with a photomultiplier unit 6, and the resulting photoelectric currents are integrated in phase with the oscillation period of the sample. Further, in FIG. 5, 7 is a PSD (phase sensitive detector), 8 a recorder, and 9 a wavelength presetter.

The prior art photometric apparatus, however, has a drawback in that the information obtained therewith represents only average properties (e.g. physical properties) of the sample in the scanning range of the light beam spot on the sample and not of those in individual microscopic areas of the sample, for example, the difference in a specific distribution or aggregation of coloring matter between microscopic areas of the sample. Now that each microscopic area is observed, it is meaningless unless a very minute change in the sample can be detected, particularly when the sample is a monomolecular film or the like. With simple amplification of signals due to microscopic areas, accurate measurement of such a change is impossible due to the effects of noise. In addition, while the light beam is desired to be as narrow as possible for the purpose of evaluating each microscopic area, it is difficult to converge the light beam sufficiently since the light beam passing through the spectroscope is spread by a prism or the like.

According to the monomolecular film forming method, it is possible to design and construct a mixed monomolecular film consisting of two or more kinds of molecules or a hetero built-up film consisting of monomolecular layers which are different in composition. An important technique for evaluating physical properties of these ultra thin films is to detect unevenness between microscopic areas of the film surfaces. For instance, it is known that in mixed monomolecular films of a merocyanine colorant substituted by a long-chain alkyl and a long-chain alkylcarboxylic acid (e.g. arachidic acid), monomers, dimers, and further J-associates of the merocyanine are present, and the distribution state of these components affects properties of the film. Therefore, the distribution state that these components are placed in, and the change in the distribution state that occurs depending on the film thickness, are interesting matters in the evaluation of physical properties of the film. However it is the present situation that information about such matters cannot be obtained as stated above with the photometric apparatus according to the prior art.

SUMMARY OF THE INVENTION

An object of the invention is to extract results of photometry on desired microscopic areas of the sample and in addition evaluate and compare accurately one microscopic area, with another one.

This and other objects of the invention are achieved with (1) a photometric apparatus comprising means for moving the beam spot of a light beam so that the track of the beam spot on the sample will form a line or plane, means for determining the positions to be examined by photometry on the sample, and means for integrating signals from each position and extracting the integrated signals as a result of photometry, and (2) a photometric method comprising the steps of moving a light beam spot on a sample, generating sampling pulses corresponding to a desired microscopic area on the track of the light beam spot, and extracting the result of photometry only during the generation of the sampling pulses.

DESCRIPTION OF THE PREFERRED EMBODIMENTS

The invention is characterized in that the photometric apparatus (hereinafter abbreviated as photometer) has means for scanning a sample with a light beam so that the track of the beam spot on the sample will form a line or plane, means for measuring at least secondary light from the sample, and means for positioning each of the microscopic areas to be examined by photometry, on the sample.

Any light source may be used in the invention that emits, for example, white rays consisting of visible rays, infrared rays, and ultraviolet rays. The spectroscope may be a conventional one. The means for measuring the secondary light is a device which receives it and derives desired results therefrom. For scanning the sample with a light beam, any means capable of shifting the sample relatively to the light beam spot in two directions may be applied, including means for moving the sample, means for moving the light beam, and means for moving both. In the invention, the secondary light includes transmitted light, reflected light, phosphorescence, or luminescence from the sample.

The means for positioning each of the microscopic areas to be examined by photometry is a device with which signals produced by receiving a beam of the secondary light are sorted according to the microscopic areas, i.e. the sources of the secondary light, which are predetermined as desired on the track of the light beam spot, and the sorted signals are taken out selectively. Therefore, by the scanning means and the positioning means, the result from measuring any of the optional areas on the scanned surface can be obtained as a product of the results in each scanning cycle and the number of scanning cycles. The photometer of the invention is also capable of receiving and measuring a variety of secondary rays including transmitted light, reflected light, phosphorescence, and luminescence by varying the position of the light source relative to the light receiving section.

Figure 1:
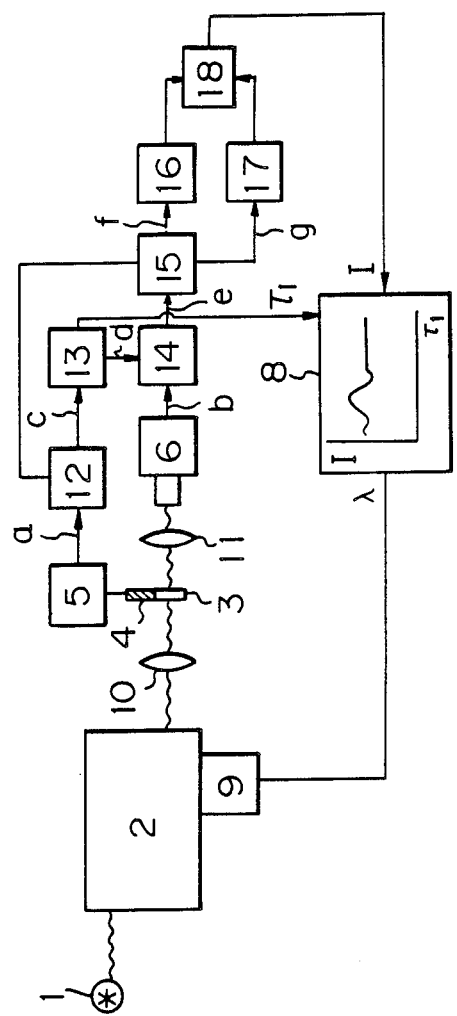
FIG. 1 illustrates an embodiment of the photometric apparatus according to the invention.

FIG. 1 is a schematic diagram showing an embodiment of the invention. This photometer operates as follows: A light beam emitted from a light source 1 is separated into monochromatic rays through a spectroscope 2. A monochromatic group of the separated rays is condensed through a lens system 10 onto a sample cell 3 and onto the sample 4 held by the sample cell 3. Secondary rays transmitted thereby are passed through a lens system 11 and sent to a photomultiplier unit 6. The sample cell 3 is oscillated at a definite cycle by means of an oscillation controlling unit 5. Thereby, the track of the light beam spots on the sample cell 3 and on the sample 4 each form a line or plane. The secondary rays entering the photomultiplier 6 are converted into photoelectric current signals b. The sample 4 is held in the upper half of the sample cell 3 and the light beam spot is reciprocally movable from a position on the sample 4-holding surface of the sample cell 3 to a position on the sample 4-non-holding surface thereof, by vertical oscillation thereof. Accordingly, the photoelectric current signals b contain sample signals based on the secondary light passed through the sample 4-holding portion and reference signals based on the secondary light passed through the sample 4-non-holding portion.

Figure 2A:
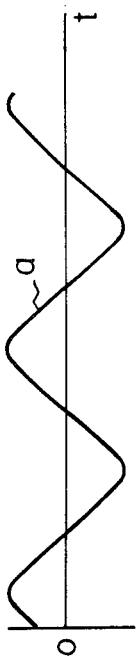
FIGS. 2(a)–2(e) show the timing of individual signals generated for photometry.
Figure 2B:
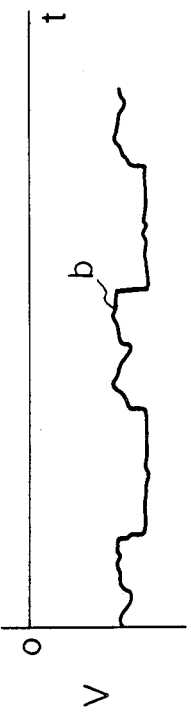

FIGS. 2(a) and 2(b) show the oscillation cycle a of the sample cell 3 and photoelectric current signals b produced from the secondary light in phase with the sample cell oscillation, respectively. In FIG. 2, t is time and V is voltage.

Figure 2C:
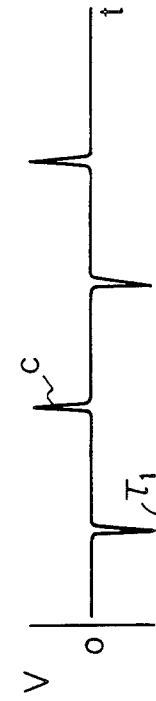
Figure 2D:
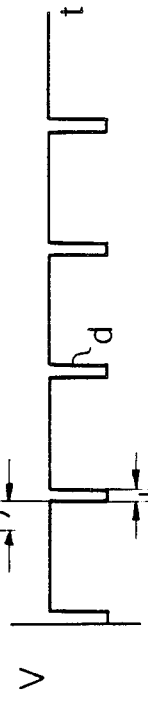
Figure 2E:
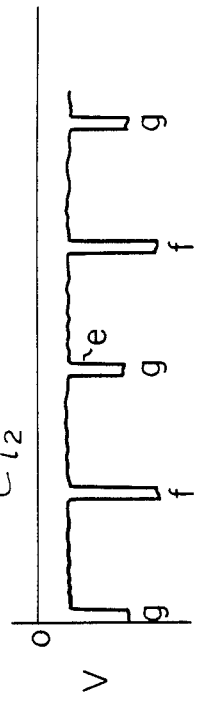

The photoelectric current signals b are integrated in phase with the oscillation over the entire area scanned on the sample according to the prior art, but on each microscopic area, according to the invention, so as to extract the measurement result on each area, by generating sampling trigger pulses from a sampling trigger unit 12 and thereby generating sampling pulses d to control the signal-sampling time. Timing of generated sampling trigger pulses c is shown in FIG. 2(c). These pulses c are delayed for an optional time (delay time) $\tau_1$ by means of a delay circuit 13 and then sent to a sampling gate 14. This gate 14 is opened for every definite moment (sampling time) $\tau_2$ by means of the sampling pulses d, shown in FIG. 2(d), produced from the sampling trigger pulses c. During the sampling times, photoelectric current signals b from the photomultiplier 6 are passed as photoelectric current signals e, as shown in FIG. 2(e), through the sampling gate 14, and amplified.

Photoelectric current signals e thus passed through the sampling gate 14 for every sampling time $\tau_2$ are separated into sample signals g and reference signals f by a discriminating circuit 15. These signals g and f are sent to integrating circuits 16 and 17, respectively, to be integrated and amplified. The photoelectric current signals e are extracted in response to each particular microscopic area on the sample cell 3 or on the sample 4 and plural times by the vertical oscillation of the sample cell 3. Accordingly, photoelectric current signals e from one microscopic area can be integrated plural times. Then, the integrated signals are converted through an arithmetic circuit 18 into a desired data signal I, e.g. transmittance or absorbance, and transmitted as a result of photometry to a recorder 8. Results of photometry can also be transmitted to a monitor TV and the like and indicated in various forms such as two-dimensional display and three-dimensional display. The reference signals f are for the purpose of removing the intervention effect of the sample cell 3 but are not always necessary depending on the nature of the secondary light.

As described above, the photometer of this embodiment has features in that (1) spectra of a sample 4 at microscopic areas can be measured by condensing light beams onto a sample cell 3 and the sample 4 and (2) spectra of the sample 4 at different microscopic areas can be evaluated separately by causing the delay time $\tau_1$ of trigger pulses c to correspond to the light beam spot movement which accompanies the oscillation of the sample cell 3 and additionally by varying the delay time $\tau_1$.

The diameter of the light beam spot can be reduced with ease to the order of 5 to 1 $\mu$m, and thereby the microscopic area to be evaluated can be reduced sufficiently. When the light beam spot is moved by the oscillation of the sample cell 3 as in this embodiment, the oscillation amplitude is desired to be in the range of approximately from 1 to 30 mm, since the oscillation in this amplitude range is possible without difficulty. The sampling time $\tau_2$ is chosen depending on the oscillation cycle T of the sample cell 3 and on the size of the light beam spot. Generally suitable sampling time $\tau_2$ is about T/100.

The sample-scanning means in this embodiment is a device constructed to move the sample cell 3 in two directions. The alternative to this means is a device for moving the light beam spot on the sample 4 in two directions in some way or other while fixing the sample cell 3. For example, the use of a rotating mirror is conceivable. In this case, the principle of photometer operation is completely the same as in the above embodiment. Such a modification brings about many advantages when physical properties of a thin film are evaluated by applying an electric or magnetic field to the sample 4 or when the sample temperature is controlled. Moreover, since the linear (one-dimensional) movement of the sample cell 3 or of the light beam spot is easier, the track of the light beam spot on the sample can be made planar easily by moving linearly both the sample cell 3 and the light beam spot so that the respective movement directions will cross each other. The entire area of the sample surface can be scanned with the light beam, for instance, by oscillating one of the sample cell 3 and the beam spot at a sufficiently short cycle as compared with the oscillation cycle of the other.

In this embodiment, independent variables are the wavelength or wavenumber of light to be sorted out by means of the spectroscope 2 and the delay time $\tau_1$. These two variables must be set independently of each other. On the assumption that the delay time $\tau_1$ is manually varied for each point, the operation of the photometer has been described above. However, it is also possible to add a system with which the delay time $\tau_1$ is varied automatically while fixing the wavelength of the light. Another possible modification of this embodiment is to adopt a multichannel discriminating and amplifying system such that the sampling gate 14 is opened in time series which are freely determined through the sampling trigger pulses c and the photoelectric current signals e passed therethrough are discriminated and amplified according to the time series. Referring to FIG. 3, this system is described below.

Figure 3A:
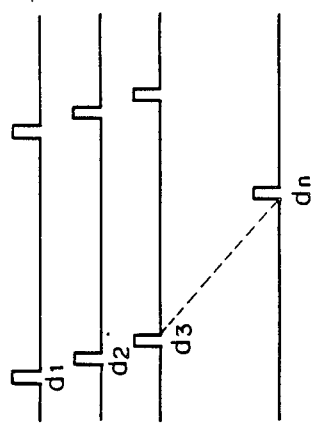
FIG. 3 illustrates another embodiment of the photometric, apparatus according to the invention, in the state of generating sampling pulses.
Figure 3B:
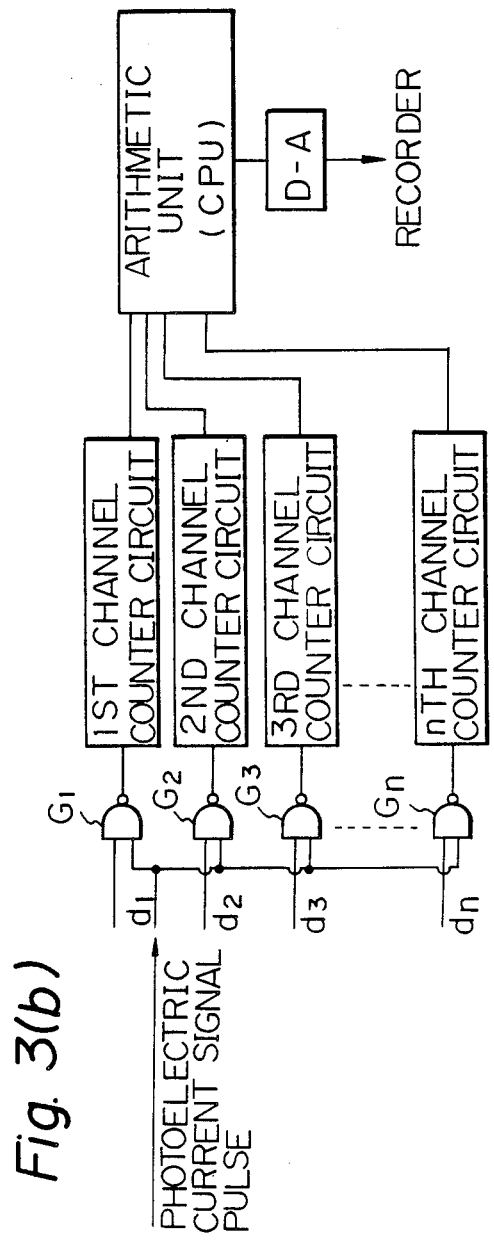

In FIG. 3(a), $d_1 \ldots d_n$ are sampling pulses, which are supplied successively in the time series freely determined by the sampling trigger pulses C, to AND circuits $G_1 \ldots G_2$ shown in FIG. 3(b). In the moments that sampling pulses $d_1 \ldots d_n$ are supplied to the AND circuits $G_1 \ldots G_n$, respectively, photoelectric current pulses b are transmitted through the AND circuits $G_1 \ldots G_n$ to the respective 1st to nth channel counter circuits, whereby the result of photometry on every microscopic area is transmitted. In this case, the results of photometry on a number of microscopic areas can be obtained by one measurement operation, thus a speed-up of measurement being possible. In such a system, digital amplification is preferred to analogue amplification and various modifications are possible such as the application of a photon counting system and utilization of a computor.

Further, the reflectance of microscopic areas can be measured in this embodiment by arranging the optical system for the incident light and the photomultiplier unit 6 on the same side of the sample 4.

Figure 4:
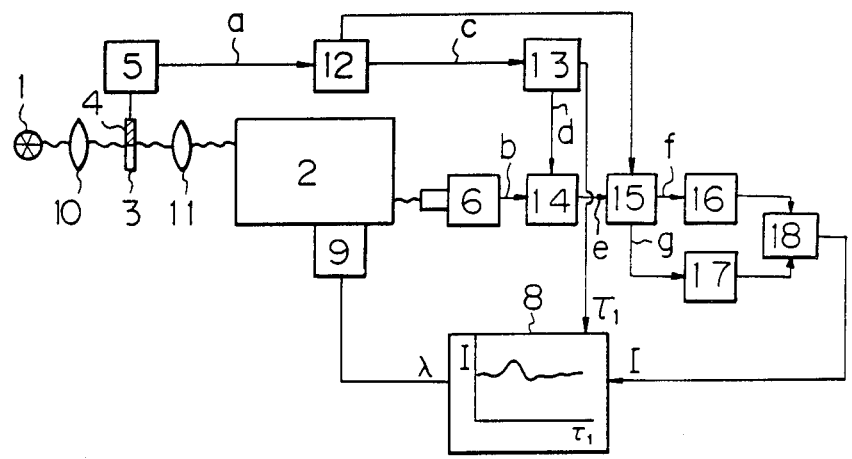
FIG. 4 illustrates another embodiment of the photometric apparatus according to the invention.
Figure 5:
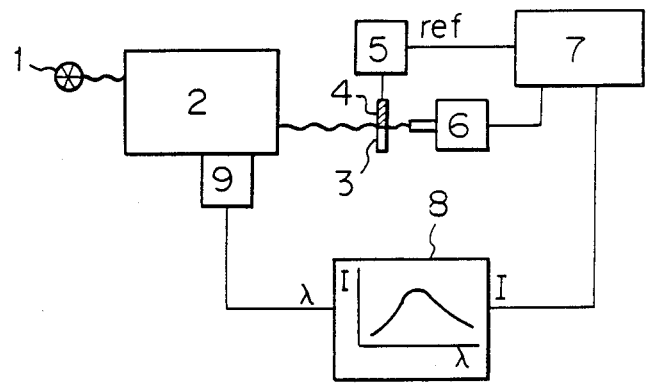
FIG. 5 illustrates a typical example of the photometric apparatus according to the prior art.

FIG. 4 illustrates another embodiment of the invention, wherein the sample 4 is irradiated with a light beam which has not been passed through spectroscope 2. Instead, secondary light passed through the sample 4 is sorted by a spectroscope 2 and then sent to the photomultiplier unit 6. Except for these points, this embodiment is the same as the one shown in FIG. 1.

The sample irradiation, in this way, with a light beam not passed through the spectroscope 2 is advantageous in that the light beam can be easily narrowed since the light beam from the light source 1 is not spread by a prism or the like in the spectroscope 2. In this case, a light beam spot of about 1 $\mu$m in diameter can be readily obtained.

As described hereinbefore, effects of the invention are that several-$\mu$m size microscopic areas of a thin film, particularly a monomolecular film, or built-up film, can be evaluated for spectra by improvements of the prior art photometric method, and that each optional microscopic area can be measured by photometry and therefore local changes in spectrum due to changes in relative position, for example, a non-uniform distribution of coloring matter, can be detected. In particular, photometric results on a specific microscopic area can be obtained by integrating signals from the area. Since a minute change can be magnified by the integration, there is no fear of inaccuracy caused by noises as in the case where signals in single scanning of the sample are merely amplified. Accordingly, the effect of the invention extends to the evaluation of thin films of high applicability, e.g. mixed monomolecular films and hetero built-up films, for uniformity and physical properties and to improvements of materials and techniques for making thin uniform films.

What is claimed is:

1. A photometric apparatus comprising:
   a light source for irradiating a sample with a light beam;
   means for oscillating a beam spot of the light beam on the sample relative to the sample, said oscillating means being driven according to an oscillation control signal;
   means for generating sampling trigger pulses in synchronization with the oscillation control signal;
   means for generating sampling pulses, the generation of each of said sampling pulses being delayed for a predetermined delay time after the generation of each of said sampling trigger pulses;
   means for measuring light from the sample; and
   means for extracting, in accordance with the sampling pulses, a photometric characteristic of a portion of the sample obtained by said measuring means.

2. A photometric apparatus according to claim 1, wherein said measuring means includes a photomultiplier unit for converting the light from the sample into photoelectric current signals, and wherein said extracting means outputs the photoelectric current signals only during the generation of said sampling pulses.

3. A photometric apparatus according to claim 1, further comprising a spectroscope disposed between said light source and the sample.

4. A photometric apparatus according to claim 1, further comprising a spectroscope disposed between the sample and said measuring means.

5. A photometric apparatus according to claim 1, wherein the diameter of the light beam from said light source is in the range of 1 to 5 $\mu$m.

6. A photometric apparatus according to claim 1, wherein the amplitude of the oscillation of the beam spot relative to the sample is in the range of 1 to 30 mm.

7. A photometric apparatus according to claim 1, wherein the light from the sample to be measured by said measuring means includes secondary light from the sample which consists of at least one of transmitted light, reflected light, phosphorescence, and luminescence.

8. A photometric apparatus according to claim 2, wherein the photoelectric current signals include sample signals and reference signals.

9. A photometric method comprising the steps of:
   irradiating a sample with a light beam;
   oscillating a beam spot of the light beam on the sample, the beam spot being oscillated relative to the sample in accordance with an oscillation control signal;
   generating sampling trigger pulses in synchronization with the oscillation control signal;
   generating sampling pulses, each of the sampling pulses being generated with a predetermined delay time after the generation of each of the sampling trigger pulses; and
   extracting, in accordance with the sampling pulses, a photometric characteristic of a portion of the sample obtained by a measuring means.

* * * * *